US007833787B2

(12) United States Patent
Otto et al.

(10) Patent No.: US 7,833,787 B2
(45) Date of Patent: Nov. 16, 2010

(54) METHOD FOR RECLONING CHINESE HAMSTER OVARY (CHO) CELLS

(75) Inventors: Ralf Otto, Oggelshausen (DE); Barbara Enenkel, Warthausen (DE); Juergen Fieder, Unterstadion (DE); Thomas Krieg, Ummendorf (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 0 days.

(21) Appl. No.: 10/922,577

(22) Filed: Aug. 19, 2004

(65) Prior Publication Data
US 2005/0059146 A1    Mar. 17, 2005

Related U.S. Application Data

(60) Provisional application No. 60/498,463, filed on Aug. 28, 2003.

(30) Foreign Application Priority Data
Aug. 19, 2003   (DE) ............................... 103 38 531

(51) Int. Cl.
C12N 5/07    (2010.01)
C12N 5/10    (2010.01)
C12N 5/00    (2010.01)
C12N 5/02    (2010.01)

(52) U.S. Cl. .................. 435/358; 435/325; 435/352; 435/373

(58) Field of Classification Search .............. 514/12; 435/358, 325, 352, 373
See application file for complete search history.

(56) References Cited

U.S. PATENT DOCUMENTS

| 5,008,198 | A |   | 4/1991 | Reese et al. |
| 5,459,058 | A | * | 10/1995 | Leder et al. ............ 435/373 |
| 2003/0032182 | A1 |  | 2/2003 | Kubota |
| 2003/0073234 | A1 |  | 4/2003 | Amit |

FOREIGN PATENT DOCUMENTS

| CA | 2 234 071 C | 5/1997 |
| CA | 2 324 479 A1 | 10/1999 |
| WO | 92/08796 A1 | 5/1992 |
| WO | 94/28143 A1 | 12/1994 |
| WO | 97/15664 A1 | 5/1997 |
| WO | 99/54435 A2 | 10/1999 |
| WO | 00/34318 A1 | 6/2000 |
| WO | 00/34326 A1 | 6/2000 |
| WO | 00/34526 A1 | 6/2000 |
| WO | 01/04306 A1 | 1/2001 |
| WO | 01/27150 A2 | 4/2001 |
| WO | WO 02/29012 A1 | 4/2002 |

OTHER PUBLICATIONS

Munzoledo et al., Cultivation, serial transfer, and differentiation of epidermal keratinocytes in serum-free medium, Biochemical and Biophysical Research Communications, 236, p. 167-172 (1997).*
Ye et al., Adult human marrow cells support prolonged expansion of undifferentiated human embryonic stem cells, Blood, Nov. 16, 2002, vol. 100, No. 11, Abstract No. 504.*
Munozledo et al., Cultivation of rabbit corneal epithelial cells in serum-free medium, Investigative Ophthamology & Visual Science, Oct. 1997, vol. 38, No. 11, 2234-2244.*
ARVO Annual Meeting Abstarct SeaRCH and pROGRAM pLANNER (2002), vol. 2002, pp. aNSTRACT No. 3158.*
Glaser. Daily Biotech Updates, Genetic Engineering, 21(11): Jun. 1, 2001, accessed online at www.genengnews.com.*
Gibco product guide for "Serum-Free and Protein-Free Media for Hybridoma Culture", Aug. 2002.*
Kunert and Katinger, from Immunotherapy for Infectious Diseases, Ed. Jacobsen, 2002, pp. 84-86.*
Bajpai et al. Mol. Reprod. Dev., pp. 1-10, 2007.*
M.J. Borrelli, et al., Evidence that the feeder effect in mammalian cells is mediated by a diffusible substance, Int. J. Hyperthermia, 1989, pp. 99-103, vol. 5, No. 1.
M. Tanner, *Dipetalonema viteae* (Filarioidea): development of the infective larvae in vitro, Acta Tropica, 38,241-249 (1981), Department of Medicine, Swiss Tropical Institute, Basel, Switzerland.
S.J. Kim et al., Abstract: Gene Expression in ES Cells Co-cultured on Reproductive Organs Originated Feeder Cells and Induced by Gonadotrophin Hormones; Society for the Study of Reproduction, Jul. 2000; abstract #312.
A. W. Huegin, Cloning of cells with autologous feeder cells, J. of Immunological Methods, 1997, 205, pp. 211-212 Elsevier Science.
S.C.G. Brezinsky et al., A simple method for enrighing populations of transfected CHO cells for cells of higher specific productivity, J. of Immunological Methods, 2003, pp. 141-155, 277, Elsevier Science.
F. L. Battye et al., Single cell sorting and cloning, J. of Immunolocical Methods, 2000, 243, pp. 25-32, Elsevier Science.
N. Borth et al., Efficient Selection of High-Producing Subclones During Gene Amplification of Recombinant Chinese Hamster Ovary Cells by Flow Cytometry and Cell Sorting, Biotechnology and Bioengineering 200-2001, V. 71 No. 4, 2000, pp. 266-273.

(Continued)

Primary Examiner—Thaian N Ton
(74) Attorney, Agent, or Firm—Michael P. Morris; Edouard G. Lebel; Paula K. Wittmayer (57) ABSTRACT

A new method for selecting clones and recloning mammalian cells which are of importance for the production of biopharmaceuticals, preferably hamster or mouse myeloma cells, with a high degree of automation and throughput. The invention relates to methods of depositing and replicating single cell clones of the cells in question. The invention also relates to methods of preparing proteins using cells which have been obtained and replicated by single cell deposition as well as compositions which allow the replication of single cells.

10 Claims, 4 Drawing Sheets

OTHER PUBLICATIONS

H. Echchakir, et al., Evidence for in situ expansion of diverse antitumor-specific cytotoxic T Lymphocyte clones in a human large cell carcinoma of the lung, The Japanese Society for Immunology, 2000, Internation Immunology, vol. 12, No. 4 pp. 537-546.

A. Hlinak, et al., Feeder Cells from Different Sources and Conditioned Media for Recloning of Human-Mouse and Mouse-Mouse Hybridomas, Int. J. Hyperthermia, 1989 vol. 5, No. 1, pp. 99-103, Folia Biologica (Praha), vol. 34, No. 2, 1998, pp. 105-117.

B. J. Green & J.E.J. Rasko, Rapid Screening for High-Titer Retroviral Packaging Cell Lines Using an In Situ Fluorescence Assay, Human Gene Therapy 13:1005-1013 (Jun. 10, 2002).

Thomas Brodin, et al; Cloning of Human Hybridoma, Myeloma and Lymphoma Cell Lines Using Enriched Human Monocytes as Feeder Layer; Journal of Immunological Methods (1983) vol. 60 pp. 1-7.

Robin N. Butcher, et al; Mitomycin C-treated 3T3/B (3T3/A31) Cell Feeder Layers in Hybridoma Technology; Journal of Immunological Methods (1988) vol. 107 pp. 245-251.

Martin Chalfie, et al; Green Fluorescent Protein as a Marker for Gene Expression; Science (1994) vol. 263 pp. 802-805.

Manfred Gossen, et al; Inducible Gene Expression Systems for Higher Eukaryotic Cells; Current Opinion in Biotechnology (1994) vol. 5 pp. 516-520.

Vitalii G. Grigoriev, et al; Senescent Fibroblasts as Feeder Cells for Lymphoid Cell Cloning; Analytical Biochemistry (1996) vol. 236 pp. 250-254.

Shi-Zhen Hu, et al; Minibody: A Novel Engineered Anti-Carcinoembryonic Antigen Antibody Fragment (Single-Chain Fv-Ch3) Which Exhibits Rapid, High Level Targetting of Xenograts; Cancer Research (1996) vol. 56 pp. 3055-3061.

James S. Huston, et al; Protein Engineering of Antibody Binding Sites: Recovery of Specific Activity in an Anti-Digoxin Single-Chain Fv Analogue Produces in *Escherichia coli*; Proc. Natl. Acad. Sci. USA ( 1988) vol. 85 pp. 5879-5883.

Hitto Kaufmann, et al; Comparative Analysis of Two Controlled Proliferation Strategies Regarding Product Quality, Influence on Tetracycline-Regulated Gene Expression, and Productivity; Biotechnology and Bioengineering (2001) vol. 72 pp. 592-602.

Alexander A. Kortt, et al; Single-Chain Fv Fragments of Anti-Neuraminidase Antibody NC10 Containing Five- and Ten-Residue Linkers Form Dimers and with Zero-Residue Linker a Trimer; Reotein Engineering (1997) vol. 10 No. 4 pp. 423-433.

William J. Long, et al; Enhancing the Establishment Efficiency of Hybridoma Cells; Journal of Immunological Methods (1986) vol. 86 pp. 89-93.

Brett Lovejoy, et al; Crystal Structure of a Synthetic Triple-Stranded α-Helical Bundle; Science (1993) vol. 259 pp. 1288-1293.

Y. Gloria Meng, et al; Green Fluorescent Protein as a Second Selectable Marker for Selection of High Producing Clones from Transfected CHO Cells; Gene (2000) vol. 242 pp. 201-207.

Peter P. Mueller, et al; Recombinant Glycoprotein Product Quality in Proliferation-Controlled BHK-21 Cells; Biotechnology and Bioengineering (1999) vol. 65 pp. 529-532.

Peter Pack, et al; Tetravalent Miniantibodies with High Avidity Assembling in *Escherichia coli*; Journal of Molecular Biology (1995) vol. 246 pp. 28-34.

Ching-An Peng, et al; Cell Growth and Differentiation on Feeder Layers is Predicted to Be Influenced by Bioreactor Geometry; ; Biotechnology and Bioengineering (1996) vol. 50 pp. 479-492.

Olga Perisic, et al; Crystal Structure of a Diabody, a Bivalent Antibody Fragment; Structure (1994) vol. 2 pp. 1217-1226.

Cristina Pintus, et al; Endothelial Cell Growth Supplement: A Cell Cloning Factor that Promotes the Growth of Monoclonal Antibody Producing Hybridoma Cells; Journal of Immunological Methods (1983) vol. 61 pp. 195-200.

Theodore T. Puck, et al; Genetics of Somatic Mammalian Cells; Journal of Experimental Medicine (1958) vol. 108 pp. 945-956.

James G. Rehinwald, et al; Serial Cultivation of Strains of Human Epidermal Keratinocytes: The Formation of Keratinizing Colonies from Single Cells; Cell (1975) vol. 6 pp. 331-344.

Berta Sanchez, et al; Cloning of Human Heterohybridoma Cell Lines Using Chronic Lymphocytic Leukemia B Cells as a Feeder Layer; Journal of Immunological Methods (1991) vol. 145 pp. 193-197.

Yona Shneyour, et al; A Simple Feeder-Layer Technique for the Plating of Plant Cells and Protoplasts at Low Density: Plant Science Letters (1984) vol. 33 pp. 293-302.

Hélène Strick-Marchand, et al; Embryonic Liver Cells and Permanent Lines as Models for Hepatocyte and Bile Duct Cell Differentiation; Mechanisms of Development (2003) vol. 120 pp. 89-98.

Gail Urlaub, et al; Deletion of the Diploid Dihydrofolate reductase Locus from Cultured Mammalian Cells; Cell (1983) vol. 33 pp. 405-412.

Justinwee Eng Lim, et al; Proteome Analysis of Conditioned Medium from Mouse Embryonic Fibroblast Feeder Layers Which Support the Growth of Human Embryonic Stem Cells; Proteomics (2002) vol. 2 pp. 1187-1203.

R. Lindsay Williams, et al; Myeloid Leukaemia Inhibitory Factor Maintains the Developmental Potential of embryonic Stem Cells; Nature (1988) vol. 336 pp. 684-687.

Noel Quinlan, et al; Enhanced Cloning Efficiencies of Murine Hybridomas Using Human Plasma Supplemented Medium; Journal of Immunological Methods (1994) vol. 171 pp. 253-258.

Morgan et al. Animal Cell Culture, Heidelberg : Spektrum, Akad. Verl. 1994, Chapter 9.1.3. p. 116 [With English Version (pp. 81-83)].

Linzhao Gheng, et al; Human Adult Marrow Cells Support Prolonged Expansion of Human Embryonic Stem Cells in Culture: Stem Cells (2003) vol. 21 pp. 131-142.

International Search Report for PCT/EP2004/009204 mailed Jul. 12, 2005.

Peter Pack, et al; Improved Bivalent Miniantibodies, with Identical Avidity as Whole Antibodies, Produced by High Cell Density Fermentation of *Escherichia coli*; Biotechnology (1993) vol. 11 pp. 1271-1277.

C.E. Rexroad, et al; Culture of Blastomeres From In Vitro-matured, Fertilized, and Cultured Bovine Embryos; Molecular Reproduction and Development (1997) vol. 48 pp. 238-245.

Sara J. Morgan, et al; Cloning Techniques; Animal Cell Culture (1993) BIOS Scientific Publishers Limited ; Berlin—Oxford ; pp. 79-92.

Zanghi et al., "Serum Protects Protein-Free Competent Chinese Hamster Ovary Cells Against Apoptosis Induced by Nutrient Deprivation in Batch Culture," Biotechnology & Bioengineering, vol. 64, No. 1 (1999); pp. 108-119.

Example of a Strategy for the Adaptation of Cells to Serum-Free Medium, Adaptation Process, http://www.cepower.ch/Bilder/SF_Strategie_Eng.pdf (Article in English & German), 2004.

* cited by examiner

METHOD FOR RECLONING CHINESE HAMSTER OVARY (CHO) CELLS

RELATED APPLICATIONS

This application claims priority benefit of U.S. Ser. No. 60/498,463, filed Aug. 28, 2003, and German Application No. 103 38 531, filed Aug. 19, 2003, each of which is hereby incorporated by reference in its entirety.

FIELD OF THE INVENTION

The present invention relates to the field of cell culture technology and concerns methods for replicating/cloning cells, preferably cell lines, which are of importance for the production of biopharmaceuticals. The invention also relates to methods for preparing proteins using cells which have been obtained and replicated by individual cell depositing, and also compositions which allow replication of individual cells.

BACKGROUND TO THE INVENTION

For the biotechnological production of biologically active or therapeutic proteins in mammalian cells, so-called biopharmaceuticals, the corresponding mammalian cells are stably transfected with DNA which codes for the biologically active protein (or its subunits). After the transfection process a pool of millions of differently transfected cells is normally obtained. Therefore the crucial step for the preparation of efficient production cell lines is in the selection and replication of cell clones which on the one hand grow very stably and on the other hand show a high specific productivity of therapeutic protein (product formation etc.). As there are millions of different product-expressing cells, it is critical to be able to analyse a plurality of cells individually with a high throughput and to use automation in order to be able to sort out suitable candidates (single cell clones) which both grow very robustly and also yield high product titres. This process of single cell isolation and subcultivation is known as cloning or recloning.

Transfected cells may be selected by fluorescence-activated cell sorting (FACS) for example, by linking the expression of the therapeutic protein to the expression of a marker protein. For this purpose for example fluorescent proteins and the variants thereof of *Aequorea victoria*, *Renilla reniformis* or other species, including but not limited to the red, yellow, violet, green fluorescent proteins or the variants thereof of non-bioluminescent organisms such as e.g. *Discosoma* sp., *Anemonia* sp., *Clavularia* sp., *Zoanthus* sp. may be co-expressed in a cell together with the therapeutic protein. Conclusions may be drawn from the fluorescence intensity as to the specific productivity and the growth characteristics of the cells.

However, there is the problem of depositing typical recombinant production cells such as mouse myeloma (NS0), hamster ovary (CHO), or hamster kidney cells (BHK), particularly if they are adapted to growth in serum-free suspension cultures, i.e. under modern production-relevant cell culture conditions, individually in culture vessels, e.g. in the wells of microtitre plates, under serum-free culture conditions, and effectively replicating (recloning) them. If only a few cells, for example less than 5 cells, are deposited in a culture vessel under serum-free conditions, these cells cannot replicate at all, or at least cannot replicate efficiently. The reason for this is suspected to be the absence of cell-to-cell contacts, a greater nutrient/growth factor requirement at a lower cell density and/or the absence or very low concentration of diffusible signal and conditioning factors.

In the prior art the problem of serum-free single cell cloning in the above-mentioned recombinant production cells is avoided by generating cell clones by the limited dilution method. In this, a minimum of 5 to 10 cells are seeded in serum-free medium in a culture dish and then subpassaged by repeated dilution cloning in order to obtain, in statistical terms, a culture consisting of genetically identical cells (method=limited dilution). On the one hand this method of recloning is time-consuming and on the other hand it usually leads to genetically heterogeneous mixed cultures, as the process is based on a statistical calculation and not on actual cultivation of individually deposited genetically identical cells. These heterogeneous mixed cultures are generally characterised by limited robustness with respect to fermentation and a heterologous expression profile.

Alternatively, at present, single cell clones of production-relevant cell lines can only be generated by the individual depositing of serum-adapted adherent cells. Thus, Meng et al., (Meng Y G., et al., Gene 2000, 242, 201-207) mention, for example, a method of depositing individual, adherently growing CHO cells in serum-containing medium. The method described by Meng et al., however, has major disadvantages; i.e., because of the adherence of the cells, the laborious enzymatic detachment of the cells from the substrate (trypsin treatment) may lead to considerable cell damage and changes in the growth characteristics and in the productivity of the recloned cells. Moreover, the correspondingly obtained individual clones then have to be adapted to serum-free growth in suspension culture, which is normally a time-consuming operation and affects the productivity of the cells and the product quality (cf. on this subject, inter alia, Kaufmann H. et al., Biotechnology and Bioengineering 2001, 72, 592-602; Mueller et al., Biotechnology and Bioengineering 1999, 65, 529-532).

By using nutrient cells, also known as feeder cells, in the cultivation of adherently growing cells, it is possible to influence the growth characteristics of cells for the better or, for some types of cell, to replicate them under cell culture conditions for the first time. Examples include human-mouse or mouse-mouse hybridoma cells (Hlinak A. et al., Folia Biologica (Praha) 1988, 34, 105.117, U.S. Pat. No. 5,008,198), primary keratinocytes (Rheinwald, J G and Green, Cell 1975, 6, 331-344; WO 9954435), stem cells (Williams R L., et al., Nature 1988, 336, 684-687) and various tumour cells (Wee Eng Lim et al., Proteomics 2002, 2, 1187-1203; Rexroad et al., Molecular Reproduction and Development, 1997, 48, 238-245; Peng et al., Biotechnology and Bioengineering, 1996, 50, 479-492; Grigoriev et al., Analytical Biochemistry, 1996, 236, 250-254; Sanchez et al., Journal of Imunological Methods, 1991, 145, 193-197; Butcher et al., Journal of Immunological Methods, 1988, 107, 245-251; Long et al., Journal of Immunological Methods, 1986, 86, 89-93; Shneyour et al., Plant Science Letters, 1984, 33, 293-302; Pintus et al., Journal of Immunological Methods, 1983, 61, 195-200; Brodin et al., J Immunological Methods, 1983, 60(1-2),1-7). Feeder cells are usually cells the growth of which has been chemically or physically arrested, which have lost their capacity for cell division as the result of a special pre-treatment but otherwise still remain vital for about 2 to 3 weeks on average. Feeder cells are thus still capable of releasing growth-promoting factors into the medium and can thus promote the initial growth of non-arrested cells or even make this growth possible, in the case of various primary cells. For this purpose the feeder cells are plated out in a culture dish as a so-called monolayer. Then the adherently growing cells which are to be cultivated are plated out on or between the feeder cells and cultivated under standard conditions. Feeder cells may be prepared for example by irradiation or treatment with mitomycin C (azirino[2',3':3,4]pyrrolo[1,2-a]indole-4,7-dione,6-amino-8-[[(aminocarbonyl)oxy]methyl]-1,1a,2,8,8a,8b-hexahydro-8a-methoxy-5-methyl-, [1aR-(1a.alpha.,8.beta.,8a.alpha.,8b.alpha.)]-(9Cl) (Butcher et al., Journal of Immunological Methods, 1988, 107, 245-251)). Primary cells such as spleen cells, fibroblasts, blood cells (Morgan, Darling; Kultur tierischer Zellen [culture of animal cells]. Spektrum Akademischer Verlag 1994, p. 115f) and macrophages (Hlinak A. et al., Folia Biologica (Praha) 1988, 34, 105.117) have been described in feeder cell systems. In connection with the production of antibodies in hybridoma cells the use of feeder cells and FACS-based cell selection was described. Hlinak et al. (1988) for example describe a recloning efficiency of 33 to 57% in the reckoning of adherently growing hybridoma cells starting from two (2) cells per culture dish. The hybridoma cells used were adherently growing cells adapted to serum-containing medium.

When using heterologous, particularly human feeder cells for generating production cells there is a considerable risk of contamination by pathogens such as, for example, viruses, bacteria or mycoplasms. Moreover, many of the (primary) feeder cells described require serum-containing medium, which firstly increases the risk of contamination and secondly has the drawback that production cells which have laboriously been adapted to serum-free growth have to be re-adapted.

When using heterologous feeder cells, it is generally necessary to counter-select the feeder cells. Production cells are generally subject to a selection pressure, e.g. as a result of the use of additives to the medium (antibiotics such as G418) and/or incomplete media (absence of hypoxanthine, thymidine). This selection pressure makes it possible to select cells, for example, which have absorbed and integrated the corresponding genetic information for a recombinant protein. The medium thus produced which is adapted to the production cell critically influences the growth of the feeder cells and together with the otherwise incompatible production medium leads to a very rapid dying off of the feeder cells. As a result, the function of the feeder cells is no longer guaranteed.

SUMMARY OF THE INVENTION

One aim of the present invention was to find an efficient recloning method which allows production-relevant mammalian cells to be replicated under serum-free conditions and in suspension culture, starting from less than five cells, preferably from one (1) single cell. In particular, the aim was to provide corresponding processes for recloning CHO or BHK cells originally isolated from hamsters and myeloma cells originally isolated from mice, e.g. NS0 cells.

A further aim of the invention was to provide compositions which make it possible to carry out the corresponding recloning methods, particularly those for recloning hamster or mouse myeloma cells.

These objectives are achieved by means of the objects according to the invention as defined in the patent claims, which according to one aspect of the invention relates to a method for cloning cells, characterised in that fewer than five, preferably one (1) or two (2) mammalian cell(s), preferably hamster or mouse myeloma cells, are deposited in the presence of feeder cells, preferably of autologous origin, in a culture vessel under serum-free conditions and cultivated and replicated under serum-free conditions. One particular aspect of the invention relates to a corresponding process for recloning CHO or BHK cells (hamster cells) or NS0 cells (mouse myeloma cells), preferably when the cells are those which are adapted to serum-free growth in suspension cultures.

Another embodiment of the invention relates to the use of hamster cells as feeder cells in the event that the mammalian cells which have been deposited and are to be cloned are also hamster cells, particularly CHO or BHK cells. Mouse myeloma cells are preferably used as feeder cells if the cells which have been deposited and are to be cloned are NS0 cells.

In another aspect, the invention relates to a corresponding process for reckoning CHO, BHK or NS0 cells, which is characterised in that CHO cells are used as feeder cells if the mammalian cells to be cloned are CHO cells, in that BHK cells are used as feeder cells when the mammalian cells to be cloned are BHK cells, and that NS0 cells are used as feeder cells when the mammalian cells to be cloned are NS0 cells.

The processes according to the invention are characterised by a good recloning efficiency of more than 10%, preferably more than 20%, particularly for individually deposited cells. According to another embodiment the recloning methods according to the invention have a recloning efficiency of more than 30%, preferably more than 40%, particularly preferably more than 50%, more preferably more than 60%, even more preferably more than 70%, yet more preferably more than 80%.

In this case recloning efficiencies from 10 to more than 65% (e.g., at least 10%, at least 20%, at least 30%, at least 40%, at least 50%, at least 60%) in the reckoning of individually deposited CHO cells, from 10 to more than 50% (e.g., at least 10%, at least 20%, at least 30%, at least 40%, at least 50%) in the recloning of individually deposited BHK cells and from 10 to more than 45% (e.g., at least 10%, at least 20%, at least 30%, at least 40%) in the recloning of individually deposited NS0 cells, are regarded as efficient. If more than one (1) cell is deposited per culture dish, for example two, three or four, the recloning efficiency for the cells in question is above the values specified for the recloning of CHO, BHK and NS0 cells.

In another aspect the invention relates to a corresponding process for recloning mammalian cells, particularly hamster or mouse myeloma cells, wherein the cells to be cloned are replicated in the presence of 100 to 200,000 feeder cells per ml of medium.

The present invention also relates to processes for producing proteins, preferably recombinant proteins, in serum-free non-adherently growing mammalian cells which have been grown by one of the cloning methods according to the invention, particularly the production of recombinant proteins in correspondingly cloned hamster or mouse myeloma cells such as for example CHO, BHK or NS0 cells, under serum-free conditions, comprising the steps of:

a) culturing mammalian cells which express a gene product of interest, under serum-free conditions, which allow the cells in question to replicate;
b) depositing less than five (5), preferably one (1) or two (20 of the corresponding mammalian cells in one cell culture vessel under serum-free conditions;
c) replicating the correspondingly deposited cells in the presence of autologous feeder cells under serum-free conditions;
d) cultivating the replicated deposited cells under serum-free conditions under which the gene of interest is expressed; and
e) recovering and purifying the gene product which is coded by the gene of interest from the cells including the membrane or from the culture supernatant.

The expression of a recombinant gene product also requires the transfection of the mammalian cells with a nucleic acid which codes for the gene product of interest.

The mammalian cells can, for example, be separated manually or by FACS-based sorting and deposited in a cell culture vessel with feeder cells. Preferably non-adherently cultivated feeder cells are used.

The present invention also relates to the fundamental use of hamster cells, preferably CHO or BHK cells and mouse myeloma cells, preferably of type NS0, as feeder cells. According to a preferred embodiment, the present invention relates to the use of corresponding cells adapted to serum-free culture conditions.

The present invention also relates to compositions consisting of a serum-free cell culture medium, fewer than five mammalian cells capable of dividing and feeder cells autologous with the divisible mammalian cells. According to a further aspect of the invention, the divisible mammalian cells are cells which are adapted to serum-free growth as a suspension culture. In a particular embodiment the composition contains only one (1) or two (2) mammalian cells capable of dividing in the culture medium. The divisible mammalian cells are preferably hamster cells such as for example CHO or BHK cells, or mouse myeloma cells, e.g. NS0 cells.

According to another aspect of the invention, the composition contains hamster cells, preferably CHO cells as feeder cells if the divisible mammalian cell(s) are CHO cells. If the divisible mammalian cell(s) are BHK cells, the composition also contains hamster cells, but preferably BHK cells as feeder cells. If the divisible mammalian cell(s) are mouse myeloma cells, for example NS0 cells, the composition also contains mouse myeloma cells as feeder cells, and in the case of NS0 cells preferably also contains NS0 cells as feeder cells.

Surprisingly, it has been found that by using suspended autologous feeder cells, single mammalian cells, preferably hamster or mouse myeloma cells, can be deposited in serum- and/or protein-free medium and grow into cultures and thus the above-mentioned disadvantages of recloning, for example by limited dilution, or the adaptation of monoclonal cell lines to serum-free growth in suspension culture can be overcome.

The process according to the invention makes it possible to deposit corresponding mammalian cells in cells in serum-free, protein-free or chemically defined production medium, so that there is no need to carry out adaptation to serum-free or protein-free production medium, as would normally be required. This leads to a substantial shortening of development times (about 50%) in establishing production-relevant cell lines. Moreover, the deposition of single cells leads to stable, homogeneous cell clones, which is of crucial importance in the production of biopharmaceuticals, not least with regard to regulatory requirements in their licensing as drugs. Furthermore, the use of autologous feeder cells for the recloning of production-relevant CHO, BHK or NS0 cells, e.g. the use of hamster cells, preferably CHO or BHK cells, or mouse myeloma cells, preferably NS0 cells, has a considerably lower risk of contamination with regard to human pathogens than the use of human or less well-characterised cells.

DESCRIPTION OF THE FIGURES

FIG. 3b is based on the data shown in FIG. 3a. The percentage probability of obtaining a producer with double the average productivity (=high producer) is shown. A normal distribution was matched to the data obtained for all the living cells and the average titre was determined. Then, the percentage at which the cell clones obtained by individual cell deposition have double the titre or more was calculated from the distribution function for normal distribution. This percentage is shown in FIG. 3b. The graph shows that the probability of a high producer when additionally using the top 5% criterion compared with the use of the criterion "living cell" on its own increases more than twenty-fold.

DETAILED DESCRIPTION OF THE INVENTION AND PREFERRED EMBODIMENTS

Before the more detailed description of the invention by means of the non-restrictive exemplifying embodiments that follow, it should be pointed out that the use of the indefinite article, for example "a" or "an" and the definite article, namely "the", includes both the singular and plural of the term in question, unless one of the two forms is explicitly ruled out and reference is made to a particular form (singular or plural). Thus, the term "a cell" automatically includes "a plurality of cells" as well, unless it is explicitly stated that only a single cell is meant. The singular is explicitly meant, for example, where "a" or "one" is supplemented by (1).

Definitions

The term "cloning/recloning", "clone/recline" in connection with cell culture means a technique by means of which a cell population of identical cells can be obtained from an original cells. The term "cell cloning" or "single cell cloning" thus means a process wherein single cells can be identified and isolated from a cell pool with cells of different genotypes and then replicated to form a cell population consisting of a plurality of genetically identical cells. If the cells are deposited individually, i.e. only one (1) cell per culture vessel, and then expanded to form a cell population of identical cells, the process is "direct single cell cloning". If a number of cells are simultaneously deposited in a culture vessel, expanded to form a cell population and this is divided up into cell populations of identical cells by repeated dilution (=limited dilution), this is described as an "indirect cloning" method.

Single clones are genetically identical cells which originate from one (1) single cell. A cell population consisting of identical cells of the same origin is consequently referred to hereinafter as a "monoclonal cell population". If during the cultivation of cells of the same origin there are spontaneous changes in the genome, for example mutations and/or translocations, the individual cells of this cell population are still regarded as identical cells for the purposes of the present invention, and the culture is regarded as a monoclonal cell population. By contrast, a pool of stably transfected cells (transfectants) are not cell clones of the same lineage, i.e. they are not a monoclonal cell population, even if genetically identical starting cells are transfected with an identical nucleic acid.

The term "subclones/subcultures" refers to different generations of cells which are produced from an original cell or original culture by single or multiple passaging of the dividing cells. The words "subclones/subcultures" are used, for example, when identical cells or cell cultures are cultivated and replicated over a number of generations.

By "effective or efficient recloning" is meant a cloning efficiency of at least 10%, preferably at least 20%, more preferably at least 30% and even more preferably at least 40%. According to a particularly preferred embodiment of the present invention the term effective recloning means cloning with an efficiency of at least 50%, preferably at least 60%, most preferably at least 70% and even more preferably at least 80%.

The term "cloning efficiency" is defined as the percentage of cells which can form vital cell populations of preferably more than 50 cells after being deposited. If for example in a cell sorting operation 50 cells are distributed over 50 culture vessels and if 25 of these 50 individually deposited cells grow to form cultures, the cloning efficiency is 50% (25 out of 50).

The term "capable of division/expandable" for the purposes of the present invention describes the potential of a cell/cell population to divide endlessly but at the least over 2, preferably 4, passages. This potential may for example by reduced or destroyed altogether by irradiation with $^{137}$Cs or by mitomycin C treatment.

The term "derivative/descendant" refers to cells which can be traced back genetically to a particular starting cell and are formed for example by subcultivation (with or without selection pressure) and/or generated by gene manipulation. Re-isolations of cells of the same cell type are also included in the term "derivative/descendant". Thus, for example, all CHO cell lines are derivatives/descendants of the hamster ovary cells isolated from *Cricetulus griseus* by Puck et al., 1958, regardless of whether they were obtained by subcultivation, re-isolation or gene manipulations.

The term "autologous feeder cell" means that both the feeder cell and the cell which is to be cultivated in the presence of this feeder cell are derived taxonomically from the same origin. If for example the cell to be cultivated is a hamster cell (subfamily *Cricetinae*), preferably a cell of the genus *Cricetulus* or *Mesocricetus*, for example a CHO or BHK cell, each feeder cell originally isolated from this subfamily is a feeder cell which is autologous to these hamster cells of the subfamily Cricetinae. According to a preferred embodiment the term "autologous feeder cell" means that both the feeder cell and the cell which is to be cultivated were derived from the same genus taxonomically or were originally isolated from the same genus (cells from *Cricetulus* or *Mesocricetus*). If for example the cell to be cultivated is a hamster cell of the genus *Cricetulus* or *Mesocricetus*, preferably a CHO or BHK cell, each feeder cell originally isolated from the genus in question is an autologous feeder cell in the sense of this invention. According to another preferred embodiment an autologous feeder cell is present if the feeder cell and the cell to be cultivated come from the same species, for example *Cricetulus griseus* or *Mesocricetus auratus*. According to a particularly preferred embodiment an autologous feeder cell is present if both the feeder cell and the cell to be cultivated come from the same species and have the same tissue tropism (e.g. ovarian cells from *Cricetulus griseus*—CHO cells). According to a particularly preferred embodiment, a feeder cell is an autologous feeder cell if both the feeder cell and the cell to be cultivated originate from the same basic cell, for example if both cells were originally CHO-DG44 cells or descendants of these cells. According to another preferred embodiment the feeder cell confers the same resistances, e.g. to antibiotics, as the cell which is to be cultivated. This is particularly advantageous when the cell deposition is carried out in the presence of a selecting agent, e.g. an antibiotic.

The term "serum-free" means culture media and also cultivation conditions which are characterised in that cells are grown in the absence of animal and/or human serum, preferably in the absence of any proteins isolated from serum, preferably in the absence of non-recombinantly produced proteins. Consequently, the term "cells adapted to serum-free conditions" means those cells which can be replicated in the absence of animal or human serum or serum proteins.

The term "protein-free" means that the culture medium does not contain any animal proteins; proteins isolated from bacteria, yeasts or fungi are not regarded as animal proteins.

The term "chemically defined" describes a cell culture medium which is serum-free, preferably also protein-free, and which consists of chemically defined substances. Chemically defined media thus consist of a mixture of predominantly pure individual substances. One example of a chemically defined medium is the CD-CHO medium produced by Messrs Invitrogen (Carlsbad, Calif., US).

The expression "a cell which may be cultivated in suspension" refers to cells which are adapted to growth in liquid cultures ("suspension cultures") and whose ability to adhere to the surfaces of vessels, for example cell culture dishes or flasks, has been restricted or lost. Cells which are adapted both to serum-free growth and to growth in suspension are referred to as "non-adherent cells adapted to serum-free medium". If feeder cells are prepared from such cultures, these cells are by definition "non-adherent feeder cells adapted to serum-free medium".

DESCRIPTION OF THE INVENTION

The present invention relates to a method of cloning cells, characterised in that fewer than five, e.g. four, three, two or one (1) mammalian cell(s) is or are deposited in a culture vessel in the presence of feeder cells, preferably autologous feeder cells, in a culture vessel under serum-free conditions and cultivated and replicated under serum-free conditions. According to a preferred embodiment the present invention relates to a corresponding method of cloning mammalian cells, characterised in that one (1) or two mammalian cell(s) per culture vessel is or are deposited under serum-free conditions and cultivated in the presence of autologous feeder cells under serum-free conditions. A preferred embodiment relates to a method of cloning single cells, characterised in that one (1) single mammalian cell is deposited in a culture vessel in the presence of autologous feeder cells under serum-free conditions, and cultivated and replicated under serum-free conditions. In another preferred embodiment the deposited cell which is to be cultivated is a cell growing in suspension culture.

If only one (1) cell is deposited per culture vessel and replicated to form a cell population, each individual growing cell population is a monoclonal cell population and the process is a method of direct single cell cloning. If more than one (1) single cell is deposited and replicated in each culture vessel, for example two, three or four cells, the growing cell populations are so-called mixed clones. These may then be converted into so-called statistical monoclonal cell populations by direct single cell cloning or by conventional methods, for example by repeated dilution of the cell populations (=limited dilution) (see for example Morgan, Kultur tierischer Zellen [culture of animal cells], pages 113 and 114, Spektrum Akademischer Verlag 1994).

The processes provided by the present invention can be used particularly to replicate and clone mammalian cells of the subfamily Murinae, for example of the genus *Mus* or subfamily Cricetinae, for example of the genera *Cricetulus* or *Mesocricetus*, as well as cell lines isolated from them, including their descendants/derivatives. Particularly preferred is the method of replicating/cloning hamster cells or mouse myeloma according to the invention and stable cell lines derived therefrom. Accordingly, the present invention relates to a method of cloning cells in the presence of feeder cells, preferably autologous feeder cells, characterised in that the deposited mammalian cells which are to be cloned are hamster or mouse myeloma cells.

According to a particularly preferred embodiment the processes according to the invention are methods of replicating/cloning hamster cells of the genus *Cricetulus* (Chinese dwarf hamster) and stable cell lines isolated from this genus or derived from the isolated cells, e.g. CHO, CHO-K1, CHO-DUKX, CHO-DUKX B1 or CHO-DG-44 cells and derivatives/descendants of these cell lines. Particularly preferred according to the invention is a process wherein CHO-DG-44, CHO-DUKX, and CHO-K1, particularly CHO-DG-44 and CHO-DUKX cells are replicated and cloned in the presence of autologous feeder cells. Using the processes according to the invention, cells from *Mesocricetus auratus* (Syrian hamster) and stable cell lines isolated therefrom or derived therefrom, for example BHK21 or BHK TK⁻ cells and derivatives/descendants of these cell lines may also be replicated and cloned by the processes described herein. Consequently, the present invention preferably relates to a method of replicating and cloning CHO or BHK cells, and the derivatives/descendants thereof, characterised in that fewer than five, for example four, three, two, or preferably only one (1) cell(s) is or are deposited in a culture vessel in the presence of autologous feeder cells under serum-free conditions and cultivated and replicated under serum-free conditions.

Moreover the present invention relates to a method of replicating and particularly cloning mouse myeloma cells, preferably from *Mus musculus* and stable cell lines isolated or derived therefrom, for example NS0 and Sp2/0 cells and derivatives/descendants of these cell lines. This process is also characterised in that fewer than five, for example four, three, two, or preferably only one (1) of these cells is or are deposited in a culture vessel in the presence of autologous feeder cells under serum-free conditions and cultivated and replicated under serum-free conditions.

Additional Examples of hamster and mouse cells which may be replicated and cloned according to the invention are specified in the following Table 1. In addition to derivatives and descendants of these cells/cell lines, other mammalian cells, including cell lines from humans, mice, rats, monkeys, or rodents other than mice and hamsters may be replicated or cloned by a process according to the invention.

TABLE 1

Hamster and mouse cell lines

| cell line | Accession number |
|---|---|
| NS0 | ECACC No. 85110503 |
| | ATCC CRL1827 |
| | ATCC CRL2695, 2696 |
| Sp2/0Ag14 | ATCC CRL1581 |
| BHK21 | ATCC CCL 10 |
| BHK TK⁻ | ECACC No. 85011423 |
| HaK | ATCC CCL15 |
| 225462.2 (BHK21 Derivative) | ATCC CRL8544 |
| CHO | ECACC No. 8505302 |
| CHO-K1 | ATCC CCL61 |
| CHODUKX | ATCC CRL9096 |
| (= CHO duk⁻, CHO/dhfr⁻) | |
| CHODUKX B1 | ATCC CRL9010 |
| CHODG44 | Urlaub et al., Cell 33[2], 405412, 1983 |
| CHO Pro5 | ATCC CRL1781 |
| V79 | ATCC CCC93 |
| B14AF28G3 | ATCC CCL14 |
| CHL | ECACC No. 87111906 |

According to the invention the corresponding mammalian cells are preferably established, cultivated and deposited under serum-free conditions. These steps are optionally carried out in media which are free from animal proteins/peptides and/or chemically defined. Examples of commercially obtainable media include Ham's F12 (Sigma, Deisenhofen, DE), RPMI-1640 (Sigma), Dulbecco's Modified Eagle's Medium (DMEM; Sigma), Minimal Essential Medium (MEM; Sigma), Iscove's Modified Dulbecco's Medium (IMDM; Sigma), CD-CHO (Invitrogen, Carlsbad, Calif., USA), CHO-S-SFMII (Invitrogen), serum-free CHO-medium (Sigma) and protein-free CHO-medium (Sigma). Each of these media may optionally be supplemented with various compounds, e.g. hormones and/or other growth factors (e.g. insulin, transferrin, epidermal growth factor, insulin-like growth factor), salts (e.g. sodium chloride, calcium, magnesium, phosphate), buffers (e.g. HEPES), nucleosides (e.g. adenosine, thymidine), glutamine, glucose or other equivalent nutrients, antibiotics and/or trace elements. In order to select genetically modified cells which express one or more selectable marker genes, one or more suitable selecting agents, e.g. antibiotics, may be added to the medium.

Up till now, the use of feeder cells for cultivating cells has been described in connection with the cultivation of adherently growing cells (e.g. Wee Eng Lim et al., Proteomics 2002, 2, 1187-1203; Rexroad et al., Molecular Reproduction and Development, 1997, 48, 238-245; Peng et al., Biotechnology and Bioengineering, 1996, 50, 479-492; Grigoriev et al., Analytical Biochemistry, 1996, 236, 250-254; Sanchez et al., J Immunol Methods, 1991, 145, 193-197; Butcher et al., J Immunol Methods, 1988, 107, 245-251; Long et al., J Immunol Methods, 1986, 86, 89-93; Shneyour et al., Plant Science Letters, 1984, 33, 293-302; Pintus et al., J Immunol Methods, 1983, 61, 195-200; Brodin et al., J Immunological Methods, 1983, 60(1-2),1-7). Here, adherent feeder cells are laid out in a culture vessel or on a carrier as a single layer of cells (monolayer) and the cells to be cultivated are grown on this monolayer. As the feeder cells have lost their capacity for further growth (either naturally or by artificial means) the cells which are to be cultivated can replicate without being overgrown by the feeder cells. Both the feeder cells and the cells to be cultivated are adherently growing cells.

By contrast according to another embodiment the present invention makes it possible to replicate cells growing in suspension, either using adherent autologous feeder cells or, in another preferred embodiment, using autologous feeder cells which are also kept in suspension. The use of autologous feeder cells kept in suspension is particularly preferred if both the feeder cell(s) and the cell(s) to be cultivated originate from the same basic cell, for example if both cells were originally cells which had adapted to growth in suspension. Thus, the present invention also relates to a method of replicating/cloning the mammalian cells described above, characterised in that the cells to be cultivated are deposited, cultivated and replicated in the presence of autologous feeder cells kept in suspension. Particularly preferred is a corresponding process which is characterised in that the cell(s) to be cultivated is or are cell(s) adapted to growth in suspension. Also preferred in this connection is a corresponding method of replicating/cloning mammalian cells, characterised in that the depositing of the cells and the replication of the deposited mammalian cells are carried out in a serum-free and/or protein-free and/or chemically defined suspension culture.

The number of autologous feeder cells to be used in the replication/cloning of the mammalian cells described here depends fundamentally on the nature of the mammalian cell which is to be replicated and cloned and can be determined by simple titration experiments for each type of cell. The methods of replicating/cloning mammalian cells according to the invention are carried out for example in the presence of at least more than 100 autologous feeder cells per ml of medium, preferably in the presence of 100 to 200,000 autologous feeder cells per ml of medium. In another preferred embodiment the replication/cloning of the mammalian cells is carried out in the presence of 500 to 50,000 autologous feeder cells per ml of medium. Even more preferred is a process wherein the replication/cloning of the mammalian cells is carried out in the presence of 500 to 10,000 autologous feeder cells per ml medium, preferably in the presence of 2,000 to 10,000 autologous feeder cells per ml medium.

In accordance with the definition of the term "autologous feeder cells" the present invention relates to methods of replicating/cloning mammalian cells, characterised in that hamster cells, preferably of the subfamily Cricetinae, more preferably of the genus *Cricetulus* or *Mesocricetus*, are used as feeder cells when the deposited mammalian cells which are to be replicated/cloned are CHO or BHK cells and mouse myeloma cells are used as feeder cells when the deposited mammalian cells which are to be replicated/cloned are NS0 cells. Also preferred is a process for replicating/cloning mammalian cells, characterised in that CHO cells are used as feeder cells when the deposited mammalian cells which are to be replicated/cloned are CHO cells, in that BHK cells are used as feeder cells when the deposited mammalian cells which are to be replicated/cloned are BHK cells, and in that NS0 cells are used as feeder cells when the deposited mammalian cells which are to be replicated/cloned are NS0 cells.

In the event that the deposited mammalian cells which are to be cultivated are cultivated in the presence of a selection agent, it is appropriate to use autologous feeder cells which also have the selection marker gene which confers resistance, as this can prevent the feeder cells from dying off too quickly in the presence of the selection agent. Accordingly, the present invention also relates to methods of cloning cells, particularly the above-mentioned hamster or mouse myeloma cells, characterised in that fewer than five, for example four, three, two, or one (1) of these mammalian cell(s) are deposited in a culture vessel in the presence of autologous feeder cells under serum-free conditions and is or are cultivated and replicated under serum-free conditions, the autologous feeder cells and the deposited mammalian cell(s) each having at least one selection marker gene which confers resistance to a selection agent, and at least the replication of the mammalian cell(s) to be cloned takes place under serum-free conditions in the presence of said selection agent to which both the feeder cell and the mammalian cell to be cloned are resistant.

The autologous feeder cells may be produced for example by irradiating with a radioactive source of radiation, for example by irradiation with the caesium isotope 137 ($^{137}$Cs). Irradiation with an energy dose of between 1 and 1,000 Gy is advantageous for the methods of replicating/cloning mammalian cells in the presence of autologous feeder cells as described here. It is particularly advantageous to use an energy dose of between 10 and 500 Gy, more advantageously between 20 and 200 Gy. In connection with the cloning of CHO cells it has been found that the use of autologous feeder cells, preferably CHO cells, is beneficial and leads to a high level of cloning efficiency after irradiation with an energy dose of between 1 and 500 Gy. It has proved particularly advantageous to use autologous feeder cells which have been irradiated with an energy dose of between 20 and 100 Gy, preferably about 50 Gy. Theoretically, the optimum energy dose for each cell can be determined experimentally by treating feeder cells with different overall doses of radiation and determining the cloning efficiency as a function of the dose of radiation, analogously to the method described in the examples. In addition to gamma radiation with $^{137}$Cs and $^{60}$Co (cobalt isotope 60) treatment with UV radiation, electron radiation, radioactive radiation, neutron radiation and microwave radiation are also suitable, for example.

The feeder cells may be used directly or after cryopreservation, for example in liquid nitrogen, in one of the methods of replicating/cloning mammalian cells according to the invention. Processes for cryopreserving mammalian cells are known in the art and are described by way of example in Freshney (editor), Animal Cell culture—a practical approach, IRL-Press 1986, pages 73-78, the contents of which are hereby incorporated by reference.

The present processes are suitable for replicating the deposited mammalian cells up to a density of $1 \times 10^5$ to $4 \times 10^6$/ml medium in the culture vessel in which they were originally deposited. Preferably the first passaging takes place at a cell density of $2 \times 10^5$ to $8 \times 10^5$/ml of medium, particularly at a cell density of $2 \times 10^5$ to $5 \times 10^5$/ml of medium.

The methods of replicating/cloning the mammalian cells according to the invention described here are characterised by a high level of recloning efficiency, which means that the present invention relates to processes for replicating/recloning mammalian cells, characterised in that the cloning efficiency is at least 10%, preferably at least 20%, more preferably at least 30% and even more preferably at least 40%. According to a particularly preferred embodiment the present invention relates to methods of replicating/recloning mammalian cells characterised in that the reckoning efficiency is at least 50%, preferably at least 60% and particularly preferably at least 70% and even more preferably at least 80%.

According to the Examples described herein a recloning efficiency of (including) more than 65% was obtained for CHO cells. Thus, the present invention also relates to methods of replicating/recloning CHO cells which are characterised in that the recloning efficiency in the recloning of deposited CHO cells is from 10 to more than 65%, preferably more than 20%, most preferably more than 30%, more preferably more than 40%, even more preferably more than 50%, particularly more than 60%. However, the present invention also relates to processes with somewhat lower recloning efficiencies for the cell types specified.

Moreover, the present invention relates to methods of preparing one or more products (polypeptides, proteins, nucleic acids, etc.), preferably recombinant products, in cells which are replicated/recloned according to one of the methods described above. The prerequisite is that the cell in question contains one or more genes of interest which code(s) for one or more products to be prepared. Preferably the cell in question is a CHO, BHK or NS0 cell and derivatives/descendants of these cell lines. However, it may also be any other cell, e.g. one of the cells listed in Table 1.

The gene(s) of interest to be produced may be genes which occur naturally in the host cell or they may be genes artificially introduced into the cells. By definition each sequence or gene introduced into a cell is referred to as a "heterologous sequence" or "heterologous gene" in relation to this cell, even if the sequence or gene to be introduced is identical to an endogenous sequence or an endogenous gene of the cell. For example, a hamster actin gene which is introduced into a hamster cell is by definition a heterologous gene. If this heterologous gene codes for a gene of interest it is also referred to as a "heterologous gene of interest".

A heterologous gene of interest may be introduced into the cell by various methods, for example by viral transformation, transfection or microinjection. The heterologous gene of interest may be introduced into the cell as linear DNA or as part of an expression vector. A number of eukaryotic expression vectors are known which allow multiple cloning sites for the insertion of one or more heterologous genes and their expression. Commercial suppliers include among others companies such as Stratagene, La Jolla, Calif., USA; Invitrogen, Carlsbad, Calif., USA; Promega, Madison, Wis., USA or BD Biosciences Clontech, Palo Alto, Calif., USA. The transfection of the cells with a DNA or an expression vector which code(s) for one or more genes of interest is carried out by conventional methods as described for example in Sambrook et al., 1989 or Ausubel et al., 1994. Suitable methods of transfection include for example liposome-mediated transfection, calcium phosphate co-precipitation, electroporation, polycation- (e.g. DEAE dextran)-mediated transfection, protoplast fusion, microinjection and viral infections. Preferably, stable transfection is carried out in which the DNA molecules are either integrated into the genome of the host cell or an artificial chromosome/minichromosome, or are episomally contained in stable manner in the host cell. The transfection method which gives the optimum transfection frequency and expression of one or more heterologous genes of interest in the host cell in question is preferred.

The heterologous gene of interest is usually functionally linked to a promoter which enables the transcription of the gene of interest, and to other regulatory elements which allow transcription and translation (expression) of the gene of interest or increase its efficiency.

The term "promoter" denotes a polynucleotide sequence which enables and controls transcription of the genes or sequences functionally linked to it. A promoter contains recognition sequences for binding RNA polymerase and the initiation site for transcription (transcription initiation site). In order to express a desired sequence in a certain cell type or a host cell a suitable functional promoter must be chosen. The skilled man will be familiar with a variety of promoters from various sources, including constitutive, inducible and repressible promoters. They are deposited in databanks such as GenBank, for example, and may be obtained as separate elements or elements cloned within polynucleotide sequences from commercial or individual sources. In inducible promoters the activity of the promoter may be reduced or increased in response to a signal. One example of an inducible promoter is the tetracycline (tet) promoter. This contains tetracycline operator sequences (tetO) which can be induced by a tetracycline-regulated transactivator protein (tTA). In the presence of tetracycline the binding of tTA to tetO is inhibited. Examples of other inducible promoters are the jun, fos, metallothionein and heat shock promoter (see also Sambrook, J., Fritsch, E. F. & Maniatis, T., Molecular Cloning: A Laboratory Manual Cold Spring Harbor Laboratory, Cold Spring Harbor, N.Y., 1989; Gossen, M. et al., *Curr Opi Biotech* 1994, 5, 516-520). Of the promoters which are particularly suitable for high expression in eukaryotes, there are for example the ubiquitin/S27a promoter of the hamster (WO 97/15664), SV 40 early promoter, adenovirus major late promoter, mouse metallothionein-1 promoter, the long terminal repeat region of Rous Sarcoma Virus and the early promoter of human Cytomegalovirus. Examples of other heterologous mammalian promoters are the actin, immunoglobulin or heat shock promoter(s).

For example, the promoter may be functionally linked to enhancer sequences in order to increase the transcriptional activity. For this, one or more enhancers and/or several copies of an enhancer sequence may be used, e.g. a CMV or SV40 enhancer.

The term enhancer denotes a polynucleotide sequence which in the cis location acts on the activity of a promoter and thus stimulates the transcription of a gene functionally connected to this promoter. Unlike promoters the effect of enhancers is independent of position and orientation and they can therefore be positioned in front of or behind a transcription unit, within an intron or even within the coding region. The enhancer may be located both in the immediate vicinity of the transcription unit and at a considerable distance from the promoter. It is also possible to have a physical and functional overlap with the promoter. The skilled artisan will be aware of a number of enhancers from various sources (and deposited in databanks such as GenBank, e.g. SV40 enhancers, CMV enhancers, polyoma enhancers, adenovirus enhancers) which are available as independent elements or elements cloned within polynucleotide sequences (e.g. deposited at the ATCC or from commercial and individual sources). A number of promoter sequences also contain enhancer sequences such as the frequently used CMV promoter. The human CMV enhancer is one of the strongest enhancers identified hitherto. One example of an inducible enhancer is the metallothionein enhancer, which can be stimulated by glucocorticoids or heavy metals.

Basically, the regulatory elements include promoters, enhancers, termination and polyadenylation signals and other expression control elements. Both inducible and constitutively regulatory sequences are known for the various cell types. "Transcription-regulatory elements" generally comprise a promoter upstream of the gene sequence to be expressed, transcription initiation and termination sites and a polyadenylation signal.

The term "transcription initiation site" refers to a nucleic acid in the construct which corresponds to the first nucleic acid which is incorporated in the primary transcript, i.e. the mRNA precursor. The transcription initiation site may overlap with the promoter sequences.

The term "transcription termination site" refers to a nucleotide sequence which is normally at the 3' end of the gene of interest or of the gene section which is to be transcribed, and which brings about the termination of transcription by RNA polymerase.

The "polyadenylation signal" is a signal sequence which causes cleavage at a specific site at the 3' end of the eukaryotic mRNA and posttranscriptional incorporation of a sequence of about 100-200 adenine nucleotides (polyA tail) at the cleaved 3'-end. The polyadenylation signal comprises the sequence AATAAA about 10-30 nucleotides upstream of the cleavage site and a sequence located downstream. Various polyadenylation elements are known such as tk polyA, SV40 late and early polyA or BGH polyA (described for example in U.S. Pat. No. 5,122,458).

"Translation regulatory elements" comprise a translation initiation site (AUG), a stop codon and a polyA signal for each polypeptide to be expressed. For optimum expression it may be advisable to remove, add or change 5'- and/or 3'-untranslated regions of the nucleic acid sequence which is to be expressed, in order to eliminate any potentially unsuitable additional translation initiation codons or other sequences which might affect expression at the transcription or expression level. In order to promote expression, ribosomal consensus binding sites may alternatively be inserted immediately upstream of the start codon. In order to produce a secreted polypeptide the gene of interest usually contains a signal sequence which codes for a signal precursor peptide which transports the synthesised polypeptide to and through the ER membrane. The signal sequence is often but not always located at the amino terminus of the secreted protein and is cleaved by signal peptidases after the protein has been filtered through the ER membrane. The gene sequence will usually but not necessarily contain its own signal sequence. If the native signal sequence is not present a heterologous signal sequence may be introduced in known manner. Numerous signal sequences of this kind are known to the skilled artisan and deposited in sequence databanks such as GenBank and EMBL.

Gene products of interest may include proteins/polypeptides, e.g. antibodies, enzymes, cytokines, lymphokines, adhesion molecules, receptors and the derivatives or fragments thereof, but are not restricted thereto. Generally, all polypeptides which act as agonists or antagonists and/or have therapeutic or diagnostic applications are of value.

The term "polypeptides" is used for amino acid sequences or proteins and refers to polymers of amino acids of any length. This term also includes proteins which have been modified post-translationally by reactions such as glycosylation, phosphorylation, acetylation or protein processing. The structure of the polypeptide may be modified, for example, by substitutions, deletions or insertions of amino acids and fusion with other proteins while retaining its biological activity.

Examples of proteins are insulin, insulin-like growth factor (IGF-I or IGF-II); human growth hormone (hGH) and other growth factors such as for example VEGF, EGF, TGF, for example TGF alpha and beta, including $\beta 1$, $\beta 2$, $\beta 3$, $\beta 4$ and $\beta 5$; tissue plasminogen activator (tPA); erythropoietin (EPO); thrombopoietin (TBO); cytokines, for example interleukins (IL) such as IL1, IL2, IL3, IL4, IL5, IL6, IL7, IL8, IL9, IL10, IL11, IL12, IL13, IL14, IL15, IL16, IL17, IL18; interferon (IFN)-alpha, -beta, -gamma, -omega or -tau, tumour necrosis factor (TNF) such as TNF-alpha, -beta or -gamma, CD40-ligand, Apo2-ligand/TRAIL, DR4, DR5, DcR1, DcR2, DcR3, OPG, Fas ligand; GCSF; GMCSF; MCSF; MCP1 and VEGF. Other examples are clotting factors such as factor VII, factor VIII, factor IX, von Willebrands factor; anticoagulant factors such as protein C; enekephalinase; RANTES (regulated on activation normally T-cell expressed and secreted); human macrophage inflammatory protein (MIP-1-alpha); (human) serum albumin, cell adhesion molecules, such as LFA1, Mac1, p150.95, VLA4, ICAM1, ICAM2, ICAM3, VCAM, or $\alpha V/\beta 3$ integrin including $\alpha$ or $\beta$ subunits; blood group antigens; flk2/3 receptor; OB receptor; mlp receptor; CTLA4; Apo2L receptors such as for example Apo2; Transforming Growth Factor (TGF); CD proteins, T-cell receptors; viral antigens such as for example gp120 of HIV; tumour associated antigens such as for example HER2, HER3 or HER4 receptor, rheumatoid factors, for example NGF$\beta$ or PDGF; Relaxin-A or -B chain; gonadropin; gonadropin-associated peptide; inhibin; activin; a cytotoxic T-lymphocyte-associated antigen (CTLA) or neurotophin factors such as for example BDNF, neurotrophin-3, -4, -5 or -6.

Other examples are monoclonal, polyclonal, multispecific and single chain antibodies and fragments thereof such as for example Fab, Fab', F(ab')$_2$, Fc and Fc' fragments, light (L) and heavy (H) immunoglobulin chains and the constant, variable or hypervariable regions thereof as well as Fv and Fd fragments (Chamov, S. M. et al., Antibody Fusion Proteins, Wiley-Liss Inc., 1999). The antibodies may be of human or non-human origin. Humanised and chimeric antibodies are also possible.

Fab fragments (fragment antigen binding=Fab) consist of the variable regions of both chains which are held together by the adjacent constant regions. They may be produced for example from conventional antibodies by treating with a protease such as papain or by DNA cloning. Other antibody fragments are F(ab')$_2$ fragments which can be produced by proteolytic digestion with pepsin.

By gene cloning it is also possible to prepare shortened antibody fragments which consist only of the variable regions of the heavy (VH) and light chain (VL). These are known as Fv fragments (fragment variable=fragment of the variable part). As covalent binding via the cystein groups of the constant chains is not possible in these Fv fragments, they are often stabilised by some other method. For this purpose the variable region of the heavy and light chains are often joined together by means of a short peptide fragment of about 10 to 30 amino acids, preferably 15 amino acids. This produces a single polypeptide chain in which VH and VL are joined together by a peptide linker. Such antibody fragments are also referred to as single chain Fv fragments (scFv). Examples of scFv antibodies are known and described, cf. for example Huston et al. (Huston, C. et al., Proc Natl Acad Sci USA 1988, 85 (16), 5879-5883).

In past years various strategies have been developed for producing multimeric scFv derivatives. The intention is to produce recombinant antibodies with improved pharmacokinetic properties and increased binding avidity. In order to achieve the multimerisation of the scFv fragments they are produced as fusion proteins with multimerisation domains. The multimerisation domains may be, for example, the CH3 region of an IgG or helix structures ("coiled coil structures") such as the Leucine Zipper domains. In other strategies the interactions between the VH and VL regions of the scFv fragment are used for multimerisation (e.g. dia-, tri- and pentabodies).

The term diabody is used in the art to denote a bivalent homodimeric scFv derivative. Shortening the peptide linker in the scFv molecule to 5 to 10 amino acids results in the formation of homodimers by superimposing VH/VL chains. The diabodies may additionally be stabilised by inserted disulphite bridges. Examples of diabodies can be found in the literature, e.g. in Perisic et al. (Perisic, O. et al., Structure 1994, 2, 1217-1226).

The term minibody is used in the art to denote a bivalent homodimeric scFv derivative. It consists of a fusion protein which contains the CH3 region of an immunoglobulin, preferably IgG, most preferably IgG1, as dimerisation region. This connects the scFv fragments by means of a hinge region, also of IgG, and a linker region. Examples of such minibodies are described by Hu et al. (Hu, S. et al., Cancer Res. 1996, 56 (13), 3055-3061).

The term triabody is used in the art to denote a trivalent homotrimeric scFv derivative (Kortt, A. A. et al., Protein Engineering 1997, 10 (4), 423-433). The direct fusion of VH-VL without the use of a linker sequence leads to the formation of trimers.

The fragments known in the art as mini antibodies which have a bi-, tri- or tetravalent structure are also derivatives of scFv fragments. The multimerisation is achieved by means of di-, tri- or tetrameric coiled coil structures (Pack, P. et al., Biotechnology 1993, 11, 1271-1277 and Pack, P. et al., J Mol Biol 1995, 246 (11), 28-34; Lovejoy, B. et al., Science 1993, 259, 1288-1293).

For selecting transfected cells these may additionally be transfected with one or more selectable marker genes. The literature describes a large number of selectable marker genes including bifunctional (positive/negative) markers (see for example WO 92/08796 and WO 94/28143). Examples of selectable markers which are usually used in eukaryotic cells include the genes for aminoglycoside phosphotransferase (APH), hygromycine phosphotransferase (HYG), dihydrofolate reductase (DHFR), thymidine kinase (TK), glutamine synthetase, asparagin synthetase and genes which confer resistance to neomycin (G418), puromycin, histidinol D, bleomycin, phleomycin and zeocin. These genes may be introduced into the cell together with the gene of interest or separately. Preferably they are also introduced into the cells by means of expression vectors. Correspondingly modified cells may be cultivated in the presence of one or more suitable selecting agents which selectively prefer cells in growth which contain and express a corresponding selectable marker gene.

It is also possible to select transfected cells by fluorescence-activated cell sorting (FACS), for example using bacterial β-galactosidase, cell surface markers or fluorescent proteins. The fluorescent proteins also allow FACS-based isolation of individual mammalian cells. Correspondingly detected cells can automatically be deposited in culture vessels as single cells or as a plurality of cells, e.g. using a laser, e.g. an argon laser (488 nm) and for example with a Flow Cytometer fitted with an Autoclone unit (Coulter EPICS Altra, Beckman-Coulter, Miami, Fla., USA). According to a preferred embodiment only one (1) or at most two cells are deposited in a cell culture dish containing autologous feeder cells in this way. It is particularly advantageous to deposit only one (1) individual cell. In addition, sorting may be done using magnetic beads. For this the cells are labelled, for example, using antibodies coupled to magnetic beads. This enables the cells to be sorted according to specific properties.

It is particularly advantageous to carry out FACS-based isolation of cell clones which have been deposited according to one of the processes described here and which co-express a fluorescent protein and a gene of interest. Preferably, the expression of the fluorescent protein and the gene of interest are functionally linked to each other. Such a functional link consists, for example, of the two genes being arranged close together, so that the expression rates of the two genes are correlated, e.g. after transient or stable transfection of a host cell. Such functional linking may also be obtained, for example, by the use of so-called IRES elements (internal ribosome entry site) or by RNA splicing, the two genes (gene of interest and gene of the fluorescent protein) being synthesised as bicistronic mRNA. In this way there is a direct correlation between the expression rate of the fluorescent protein and the gene of interest. The corresponding cell clones which exhibit high expression of fluorescent protein also have a high expression rate of the gene of interest, as a result of the functional linking.

The fluorescent protein may be, for example, a green, bluish-green, blue, yellow or other coloured fluorescent protein. One particular example is green fluorescent protein (GFP) obtained from *Aequorea victoria* or *Renilla reniformis* and mutants developed from them; see for example Bennett, R. P. et al., BioTechniques 1998, 24, 478-482; Chalfie, M. et al., Science 1994, 263, 802-805; WO 01/04306 and the literature cited therein. Other fluorescent proteins and genes coding for them are described in WO 00/34318, WO 00/34326, WO 00/34526 and WO 01/27150 which are incorporated herein by reference. These fluorescent proteins are fluorophores of non-bioluminescent organisms of the species Anthozoa, for example *Anemonia majano*, *Clavularia* sp., *Zoanthus* sp. I, *Zoanthus* sp. II, *Discosoma striata*, *Discosoma* sp. "red", *Discosoma* sp. "green", *Discosoma* sp. "Magenta" *Anemonia sulcata*. The fluorescent proteins used may consist of the wild-type proteins, natural or genetically engineered mutants and variants, fragments, derivatives or variants thereof which have for example been fused with other proteins or peptides. The mutations used may for example alter the excitation or emission spectrum, the formation of chromophores, the extinction coefficient or the stability of the protein. Moreover, the expression in mammalian cells or other species can be improved by codon optimisation. According to the invention the fluorescent protein may also be used in fusion with a selectable marker, preferably an amplifiable selectable marker such as dihydrofolate reductase (DHFR), for example.

The selection step can be carried out on cell populations or with cell populations/cell clones which have been pre-sorted. One or more, preferably one (1), two, three or four cells may be deposited per cell culture vessel. Preferably, the cells are deposited in serum-free medium, most preferably in chemically defined medium, in the presence of autologous feeder cells. Suitable media and methods according to the invention for depositing cells using autologous feeder cells are discussed in detail elsewhere in this application. Basically, two or more sorting steps may be carried out, and between the separate sorting steps the cells are cultivated and replicated over a particular length of time, e.g. about two weeks, as pools, in a suitable medium.

In order to produce one or more gene products of interest in the recloned cells the recloned cells are preferably grown in a serum-free culture medium and in suspension culture under conditions which allow expression of the gene of interest. If for example the gene of interest is under the control of a constitutive promoter, there is no need to add special inducers. If the expression of the gene of interest is under the control of an inducible promoter, for example, a corresponding inducer must be added to the cell culture medium in a sufficient but non-toxic concentration. The cells can be expanded as desired by multiple subpassaging and transferred into suitable cell culture vessels. The gene product(s) is or are produced as either a cellular, membrane-bound or secretory product.

The product of interest is preferably obtained from the cell culture medium as a secreted gene product. If a protein or polypeptide is expressed without a secretion signal, however, the gene product may also be isolated from cell lysates. In order to obtain a pure homogeneous product which is substantially free from other recombinant proteins and host cell proteins, conventional purification procedures are carried out. First of all, cells and cell debris are frequently removed from the culture medium or lysate. The desired gene product can then be freed from contaminating soluble proteins, polypeptides and nucleic acids, e.g. by fractionation on immunoaffinity and ion exchange columns, ethanol precipitation, reversed phase HPLC or chromatography on Sephadex, silica or cation exchange resins such as DEAE. Methods which result in the purification of a heterologous protein expressed by recombinant host cells are known to the skilled man and described in the literature, e.g. by Harris et al. (Harris et al., Protein Purification: A Practical Approach, Pickwood and Hames, eds., IRL Press, Oxford, 1995) and Scopes (Scopes, R., Protein Purification, Springer Verlag, 1988).

In another aspect the present invention therefore relates to a method of preparing one or more products in mammalian cells under serum-free conditions, characterised in that (i) mammalian cells contain a gene of interest which codes for a protein of interest; (ii) the mammalian cells are grown under serum-free conditions which allow replication of the mammalian cells; (iii) in each case fewer than five, preferably four, three, two or one (1) of these mammalian cell(s) are deposited in a cell culture vessel under serum-free conditions; (iv) the suitably deposited mammalian cells are replicated in the presence of autologous feeder cells under serum-free conditions; (v) the replicated cells are cultivated under serum-free conditions in which the gene of interest is expressed; and (vi) the gene product is then isolated from the cells or culture supernatant and purified. According to a preferred embodiment of this process, in point (iii) only one (1) or two (2) of the mammalian cells are deposited in each cell culture vessel. Particularly preferred is a process in which only one (1) single mammalian cell is deposited in point (iii). The cell deposition may be manual or automated, e.g. using FACS-based cell sorting. According to another preferred embodiment the mammalian cell is a transfected mammalian cell into which the gene of interest has been introduced. Accordingly, the present invention also relates to a method of preparing recombinant gene products, characterised in that before step (i) of the process described above the mammalian cells are transfected with a nucleic acid which at least codes for a gene of interest. Stable transfection of the corresponding mammalian cell is preferred.

As already mentioned, the present invention also relates to FACS-based sorting of individual mammalian cells and the deposition of single or multiple mammalian cells, preferably fewer than 5, more preferably 4, 3, 2 or 1 mammalian cell(s) which express a protein of interest, the cell sorting and cell deposition preferably taking place as a function of the expression rate of the fluorescent protein co-expressed in the mammalian cell, the expression of which is functionally linked with the expression of the protein of interest. Accordingly, the present invention also relates to a method of producing a recombinant protein in mammalian cells under serum-free conditions, characterised in that i) the mammalian cells are transfected with a gene which codes for a protein of interest; ii) the mammalian cells are transfected with a gene which codes for a fluorescent protein, the expression of the gene which codes for a fluorescent protein preferably being functionally linked to the expression of the gene of interest; iii) the transfected mammalian cells are grown under serum-free conditions which allow replication of the transfected cells and expression of at least the fluorescent protein; iv) in each case fewer than 5, preferably 4, 3, 2 or 1 (one) transfected mammalian cell(s) is or are deposited in a cell culture vessel with autologous feeder cells under serum-free conditions after FACS-based sorting, the FACS-based cell sorting being carried out on the basis of the expression rate of the fluorescent protein; v) the correspondingly deposited cells are replicated in the presence of the autologous feeder cells under serum-free conditions; vi) the replicated cells are grown under serum-free conditions in which at least the gene of interest is expressed; and vii) the gene product (of the gene of interest) is then isolated from the cells or from the culture supernatant and purified. According to a particularly preferred embodiment, in step iv) only one (1) individual cell is deposited and replicated per culture vessel.

Figure 3A:
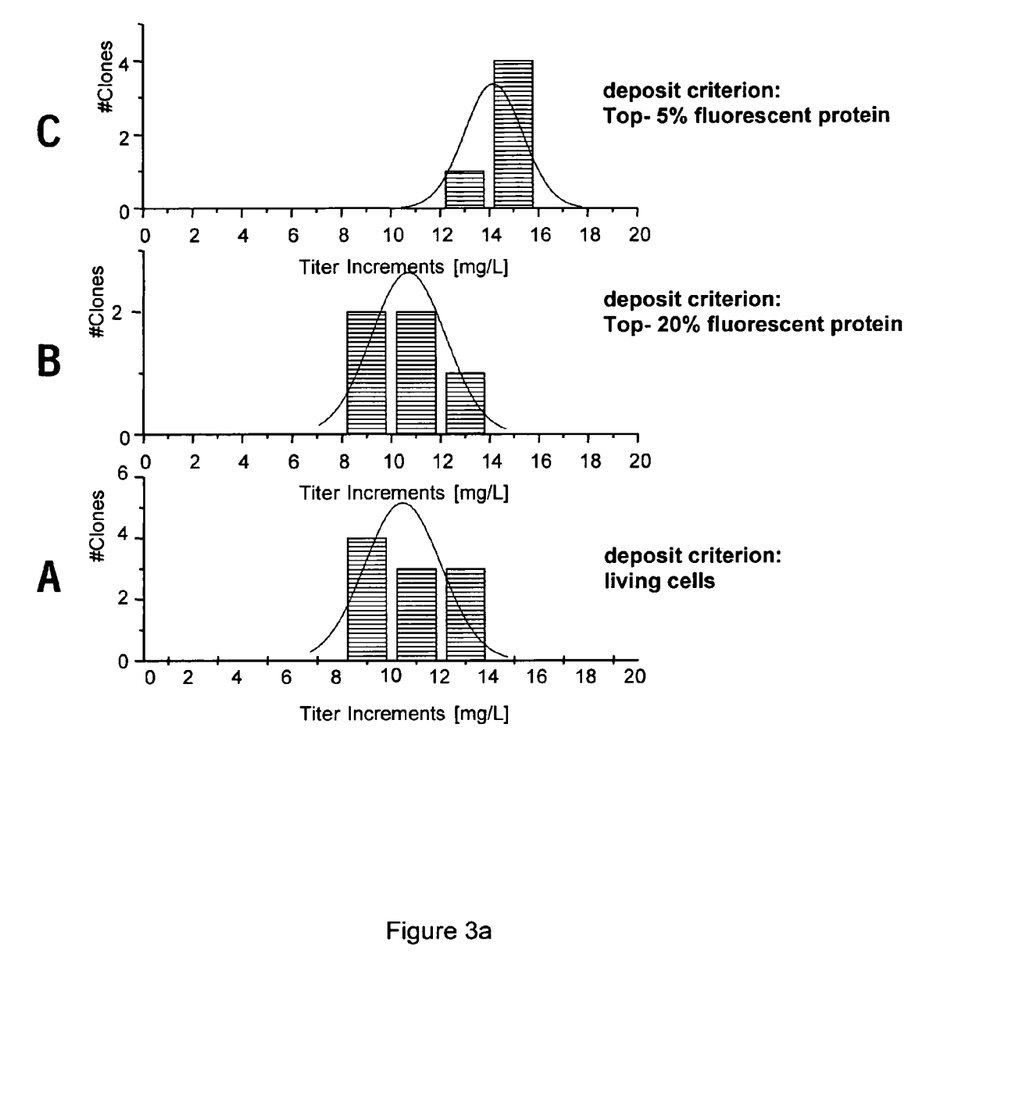
FIG. 3a shows the product titre of CHO-DG44 cell clones which have been sorted according to various criteria and individually deposited. In the bottom graph, single cells which meet only the sorting criterion "living cell" have been deposited. This criterion was defined using the Forward-Side-Scatter recording in the Flow Cytometer. The cells have not been selected by fluorescence. On the other hand, in the central and top graphs B and C the sorting criterion "fluorescence of the cells" has additionally been logically linked to the sorting criterion "living cell". The sorting criterion "fluorescence of the cells" was also further defined by means of the fluorescence intensity. To do this, on the one hand the top 20% fluorescent cell clones and on the other hand the top 5% fluorescent cell clones were individually deposited. The shift to the right in the histogram C shows that the proportion of high-expressing cell clones when using the criterion of the top 5% fluorescent cells increases significantly compared with the other sorting criteria used in A and B.
Figure 3B:
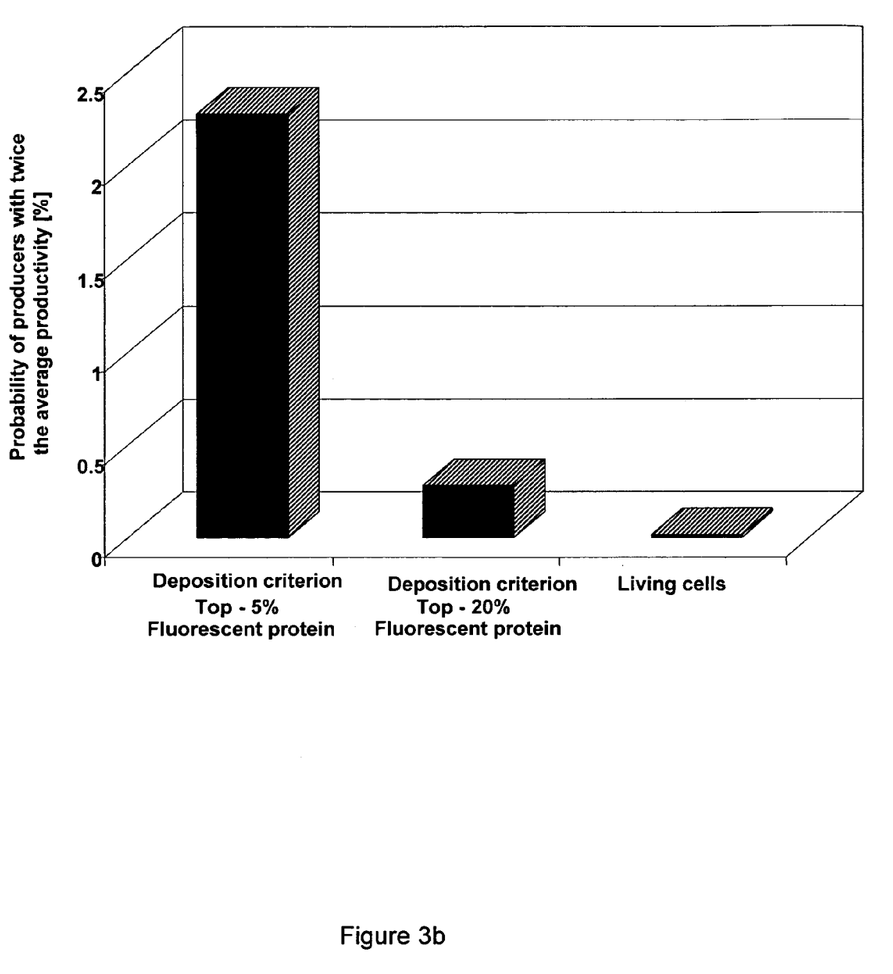

Preferably, only the cells which belong to the 20% of cells with the highest expression rate of fluorescent protein are sorted out under point iv). In practice, this means that the brightest 20% of the fluorescent cells are sorted out (20% most fluorescent cells). According to another preferred embodiment, only the brightest 5%, preferably the brightest 3%, or only the brightest 1% of the fluorescent cells of a cell mixture are sorted out. As shown in FIGS. 3a and 3b, this leads to an enrichment of cell clones with a comparatively high expression rate of the gene of interest. The FACS-based deposition of single cells thus enables identification and replication of homogeneous cell clones which have a comparatively high expression rate of a gene of interest, which in turn form the starting point for further optimising steps (e.g. gene amplification).

Also preferred is a corresponding method of producing one or more recombinant products in recloned mammalian cells, characterised in that the mammalian cells are hamster or mouse myeloma cells, preferably CHO, BHK or NS0 cells, and derivatives/descendants of these cell lines. Another embodiment of this process is characterised in that the feeder cells are adapted to serum-free medium and are non-adherently cultivated cells. Also preferred in connection with the production process described above is the use of hamster cells as feeder cells, if the deposited mammalian cell(s) which are to be replicated/cloned are CHO or BHK cells, and the use of mouse myeloma cells as feeder cells, if the deposited mammalian cell(s) which are to be replicated/cloned are NS0 cells. Particularly preferred is a process which is characterised in that CHO cells are used as feeder cells if the deposited mammalian cell(s) which are to be replicated/cloned are CHO cells, BHK cells are used as feeder cells if the deposited mammalian cell(s) which are to be replicated/cloned are BHK cells and NS0 cells are used as feeder cells if the deposited mammalian cell(s) which are to be replicated/cloned are NS0 cells.

The present invention for the first time provides hamster cells and mouse myeloma cells, preferably NS0 cells, as feeder cells. For this reason the present invention also relates to the use of a hamster cell or a mouse myeloma cell of type NS0 as a feeder cell. Methods of preparing corresponding feeder cells are described in more detail in the Examples. The corresponding hamster or mouse myeloma feeder cells can theoretically be prepared using chemical or physical methods known to the skilled man, for example by treating with mitomycin C (azirino[2',3':3,4]pyrrolo[1,2-a]indole-4,7-dione,6-amino-8-[[(aminocarbonyl)oxy]methyl]-1,1a,2,8,8a,8b-hexahydro-8a-methoxy-5-methyl, [1aR(1a.alpha.,8.beta., 8a.alpha.,8b.alpha.)]-(9Cl) (Butcher et al., J Immunol Methods, 1988, 107, 245-251) or by irradiation with $^{137}$CS. According to a preferred embodiment the present invention therefore relates to the use of chemically or physically inactivated feeder cells. The term "inactivated" means in this context that the cells are restricted in their ability to divide and have preferably lost this ability but still remain vital. This means that the cells still retain metabolic activities such as for example the synthesis and secretion of growth factors for a certain period, preferably for at least one to two weeks after inactivation. According to a preferred embodiment the corresponding feeder cells are feeder cells which are adapted to serum-free culture conditions. According to a yet more preferred embodiment of the invention the feeder cells are CHO, BHK or NS0 cells and the descendants/derivatives of these cell lines. Moreover, all the cells mentioned in this application may be used as feeder cells after being suitably inactivated.

Furthermore, the present invention relates to compositions consisting of a serum-free cell culture medium, fewer than five mammalian cells capable of dividing, preferably four, three, two or one (1) mammalian cell(s) capable of dividing and feeder cells which are autologous with the mammalian cells capable of dividing. According to a preferred embodiment of the present invention the corresponding composition contains only one (1) or two mammalian cells capable of dividing. According to another preferred embodiment the corresponding composition contains only one (1) mammalian cell capable of dividing.

Other preferred compositions contain as feeder cells hamster cells, preferably of the subfamily Cricetinae, most preferably of the genus *Cricetulus* or *Mesocricetus*, if the mammalian cell(s) capable of dividing is or are CHO or BHK cells or derivatives/descendants thereof. Moreover, another preferred composition contains, as feeder cells, mouse cells, preferably of the subfamily Murinae, most preferably of the genus *Mus*, if the mammalian cell(s) capable of dividing is or are mouse hybridoma cells, preferably NS0 cells or derivatives/descendants thereof. Particularly preferred compositions are characterised in that the composition contains CHO cells as feeder cells if the mammalian cell(s) capable of dividing is or are CHO cells, the composition contains BHK cells as feeder cells if the mammalian cell(s) capable of dividing is or are BHK cells, and the composition contains NS0 cells as feeder cells if the mammalian cell(s) capable of dividing is or are NS0 cells.

Theoretically, the invention also relates to compositions which enable fewer than 5, preferably 4, 3, 2, or 1 production-relevant hamster cell(s), such as for example CHO or BHK cell(s) and production-relevant mouse myeloma cells, such as for example NS0 cell(s) to be deposited and replicated in the presence of feeder cells from mammals under serum-free conditions.

Examples of serum-free, protein-free or chemically defined media include for example the commercially obtainable media Ham's F12 (Sigma, Deisenhofen, DE), RPMI 1640 (Sigma), Dulbecco's Modified Eagle's medium (DMEM; Sigma), Minimal Essential medium (MEM; Sigma), Iscove's Modified Dulbecco's medium (IMDM; Sigma), CDCHO (Invitrogen, Carlsbad, Calif., USA), CHO-S-SFMII (Invitrogen), serum-free CHO medium (Sigma) and protein-free CHO medium (Sigma). Each of these media can if desired be supplemented with various compounds such as hormones and/or other growth factors (e.g. insulin, transferrin, epidermal growth factor, insulin-like growth factor), salts (e.g. sodium chloride, calcium, magnesium, phosphate), buffers (e.g. HEPES), nucleosides (e.g. adenosine, thymidine), glutamine, glucose or other equivalent nutrients, antibiotics and/or trace elements. If the replicable cells are recombinant cells which express one or more selectable markers, one or more suitable selection agents such as antibiotics may also be added to the medium.

EXAMPLES

| Abbreviations | |
|---|---|
| ATCC | American Type Culture Collection |
| BHK | Baby Hamster Kidney |
| $^{60}$Co | Cobalt isotope 60 |
| $^{137}$Cs | Caesium isotope 137 |
| CHO | Chinese Hamster Ovary |
| CMV | Cytomegalovirus |
| DE | Germany |
| DEAE | Diethylaminoethyl |
| DMSO | Dimethylsulphoxide |
| DNA | Desoxyribonucleic acid |
| FACS | Fluorescence-activated cell sorter |
| FITC | Fluorescein isothiocyanate |
| Gy | Gray |
| HBSS | Hank's balanced salt solution |
| HPLC | High performance liquid chromatography |
| mRNA | Messenger ribonucleic acid |
| NS0 | Mouse hybridoma cell |
| polyA | Polyadenylation sequence |
| Sp2/0 | Mouse hybridoma cell |
| SV40 | Simian Virus No.40 |

Methods
1. Cell Culturing

The cells CHO-DG44/dhfr$^{-/-}$ (Urlaub, G. et al., *Cell* 1983, 33, 405-412) were permanently cultivated as suspension cells in serum-free CHO-S-SFMII medium (Invitrogen GmbH, Karlsruhe, DE) supplemented with hypoxanthine and thymidine in cell culture flasks at 37° C. in a humid atmosphere and 5% $CO_2$. The cell counts and viability were determined with a CEDEX Cell Counter (Innovatis, DE) or by trypan blue staining and the cells were then seeded in a concentration of $1-3 \times 10^5$/mL and passaged every 2-3 days. For the single cell cloning recombinant CHO-DG44/dhfr$^{-/-}$ were used which express a fluorescent protein (for example ZS-Green from *Zoanthus* sp.) or a fluorescent protein and a human or humanised monoclonal antibody. Cloned recombinant cells were cultured analogously to these cells. The medium used was again CHO-S-SFMII medium (Invitrogen GmbH, Karlsruhe, DE) without hypoxanthine and thymidine.

The BHK cells can be permanently cultivated as suspension cells in serum-free Opti Pro SFM medium (Invitrogen GmbH, Karlsruhe, DE) in cell culture flasks at 37° C. in a humid atmosphere under 5% $CO_2$. The cell counts and viability can be determined with a CEDEX Cell Counter (Innovatis, DE) or by trypan blue staining and the cells are then seeded in a concentration of $1-3 \times 10^5$/mL and passaged every 2-3 days. Cloned cells are cultivated analogously to the BHK cells.

The NS0 cells can be permanently cultivated as suspension cells in serum-free hybridoma medium, animal component free medium (Sigma, Aldrich, St. Louis, USA) in cell culture flasks at 37° C. in a humid atmosphere at 5% $CO_2$. The cell counts and viability can be determined with a CEDEX Cell Counter (Innovatis, DE) or by trypan blue staining and the cells are then seeded in a concentration of $1-3 \times 10^5$/mL and run every 2-3 days. Cloned cells are cultivated analogously to the NS0 cells. Hybridoma medium, animal component free medium (Sigma, Aldrich, St. Louis, USA) is used as the medium.

2. Preparation of Feeder Cells by Irradiation

Suspended CHO basic cells (non-transfected cell) growing serum- and protein-free were centrifuged for 10 minutes at 180 g and adjusted to a cell concentration of $1\times10^6$/ml in HBSS (Hank's balanced salt solution). Then, the cells were irradiated with a radioactive radiation source (Cs137 radiator, Gammacell 2000, Messrs Molsgaard Medical A/S, Denmark) with an energy dose output of 4 Gy/min. With an irradiation time of between 5 min and 125 min, an energy dose of between 20 and 500 Gy was obtained. After irradiation the cells were seeded into 96-well microtitre plates at the rate of about 2000 cells/well (=culture vessel) in the CHO-S-SFMII medium specific for the cell and stored at about 37° C. and 5% $CO_2$ in an incubating chamber atmosphere. The process is carried out in the same way with BHK and NS0 cells, the feeder cells being kept or seeded in the medium specific for the cells.

3. Cryopreservation of Feeder Cells

The feeder cells thus produced can be cryopreserved at below −150° C. The cryopreservation is carried out in the cell culture medium in question using a programmable freezer (Consarctic BV25, Consarctic, Schöllkrippen, DE). 10% (v/v) DMSO is added to the media as a cryoprotectant. The freezing rate between 0° C. and −20° C. is 1° C./min, then the temperature is lowered further at 0.4° C./min. Once freezing is complete the feeder cells are cryopreserved in liquid nitrogen in the gaseous phase.

4. Automated Cell Deposition

The automatic deposition of the cells (singly or in multiples) is carried out with a Flow Cytometer fitted with an Argon Laser (488 nm) (Coulter EPICS Altra (Messrs Beckman-Coulter, Miami, Fla., USA) using an autoclone unit. The cells are centrifuged during the exponential growth phase and taken up in HBSS to a cell concentration of $1-1.5\times10^7$/ml. Then the cells are sorted at a rate of 8000-12000 cells/second according to their position in the scattered light using the "Hypersort Option". Cells which express a fluorescent protein can alternatively be sorted according to their fluorescence intensity in relation to the intracellularly expressed fluorescent protein. The cells are deposited singly in 96-well microtitre plates containing feeder cells. BHK cells for example are deposited in OptiPro SFM medium (Invitrogen GmbH, Karlsruhe, DE). The sorted NS0 cells are deposited for example in hybridoma medium, animal component free medium (Sigma, Aldrich, St. Louis, USA). In the sorting of CHO cells the cells were deposited in CHO—S—SFM-II (Invitrogen GmbH, Karlsruhe, DE). A recombinant CHO-DG-44 cell was deposited which coexpressed a human or humanised monoclonal antibody as well as the ZS green from *Zoanthus* sp. The cell sorting was carried out as described above with an argon laser at 488 nm.

5. Determining the Productivity of Recombinantly Expressed Gene Products (for the mAb-Expressing CHO-DGH-44 Used)

The antibody titre in the supernatants from stably transfected CHO-DG-44 cells which express a human or humanised monoclonal antibody was quantified by ELISA according to standard methods (Ausubel, F. M. et al., Current Protocols in molecular biology. New York: Greene Publishing Associates and Wiley-Interscience. 1994 (updated)), using on the one hand a goat anti-human IgG Fc fragment (Dianova, Hamburg, DE) and on the other hand an AP-conjugated goat anti-human kappa light chain antibody (Sigma). The purified antibody was used as the standard. The productivities (pg/cell/day) were calculated according to the formula pg/((CtCo) t/ln (CtCo)), where Co and Ct give the cell count on seeding or harvesting and t indicates the cultivation time.

Example 1

Figure 1:
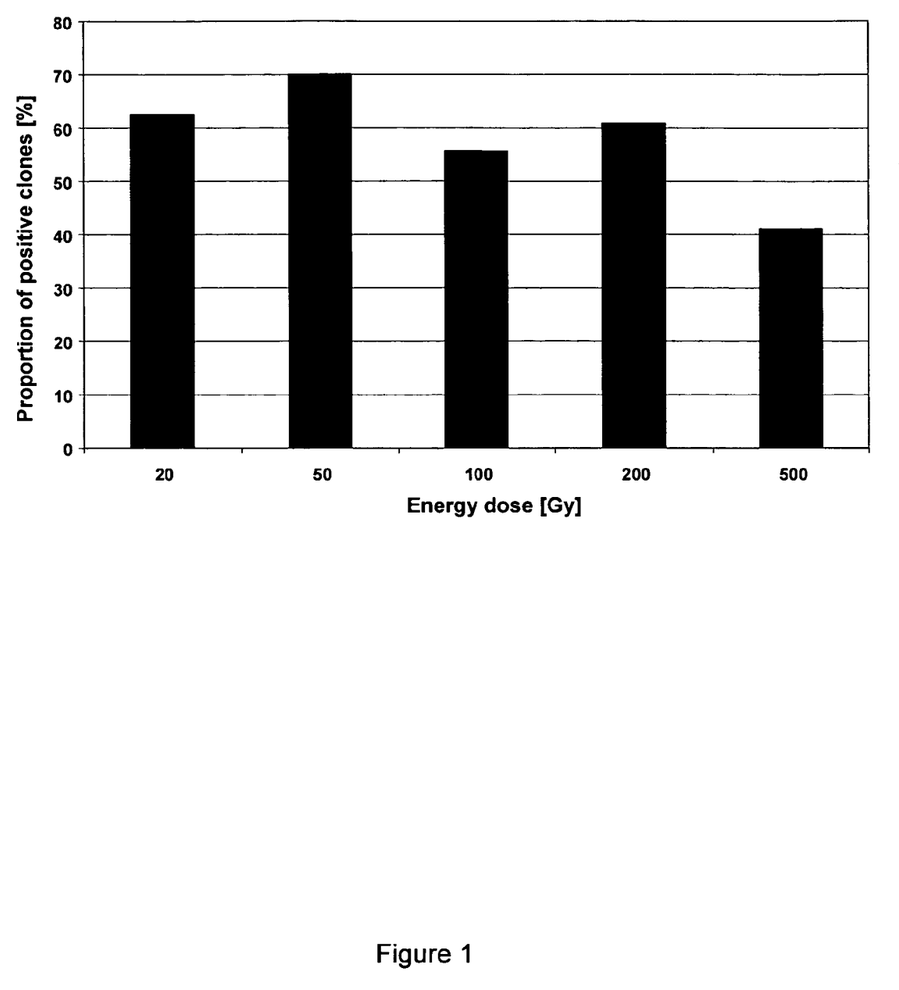
FIG. 1 shows the correlation between the dose of energy used in the production of the feeder cells and the cloning efficiency in the recloning of automatically deposited single CHO-DG44 cells. The cells are deposed in each case onto about 2000 inactive autologous feeder cells. The graphics show that feeder cells irradiated with an energy dose of 20-500 Gy still release enough factors into the medium to allow more than 65% of the single clones deposited at 50 Gy to grow into colonies.

Influence of the Energy Dose During the Production of the Feeder Cells on the Reckoning Efficiency of CHO-DG-44 Cells In order to investigate the influence of the dose of energy during the production of the feeder cells on the recloning efficiency, the CHO-DG-44 cells were grown as described under Methods "Culturing of the cells". The feeder cells were prepared as described in Methods "Preparation of feeder cells by irradiation" with an energy dose of 20 Gy, 50 Gy, 100 Gy, 200 Gy and 500 Gy. After the irradiation the feeder cells were seeded into 96-well microtitre plates with a cell count of about 2000 cells/well and stored in an incubating chamber atmosphere. Then, automated depositing of a single cell was carried out with a recombinant CHO-DG-44 cell which expressed a fluorescent protein, as described under Methods "Automated single cell deposition". One (1) individual cell was deposited on the feeder cells in each well. The target value for the recloning efficiency was the number of positive wells, i.e. the well in which there were clones which had grown to form a cell population after an incubation period of three weeks. The recloning efficiencies achieved were between 40 and 70% for the reckoning of recombinant CHO-DG44 cells (FIG. 1).

Example 2

Homogeneity of the Reckoning of Antibody-Expressing CHO-DG44 Cells

Figure 2:
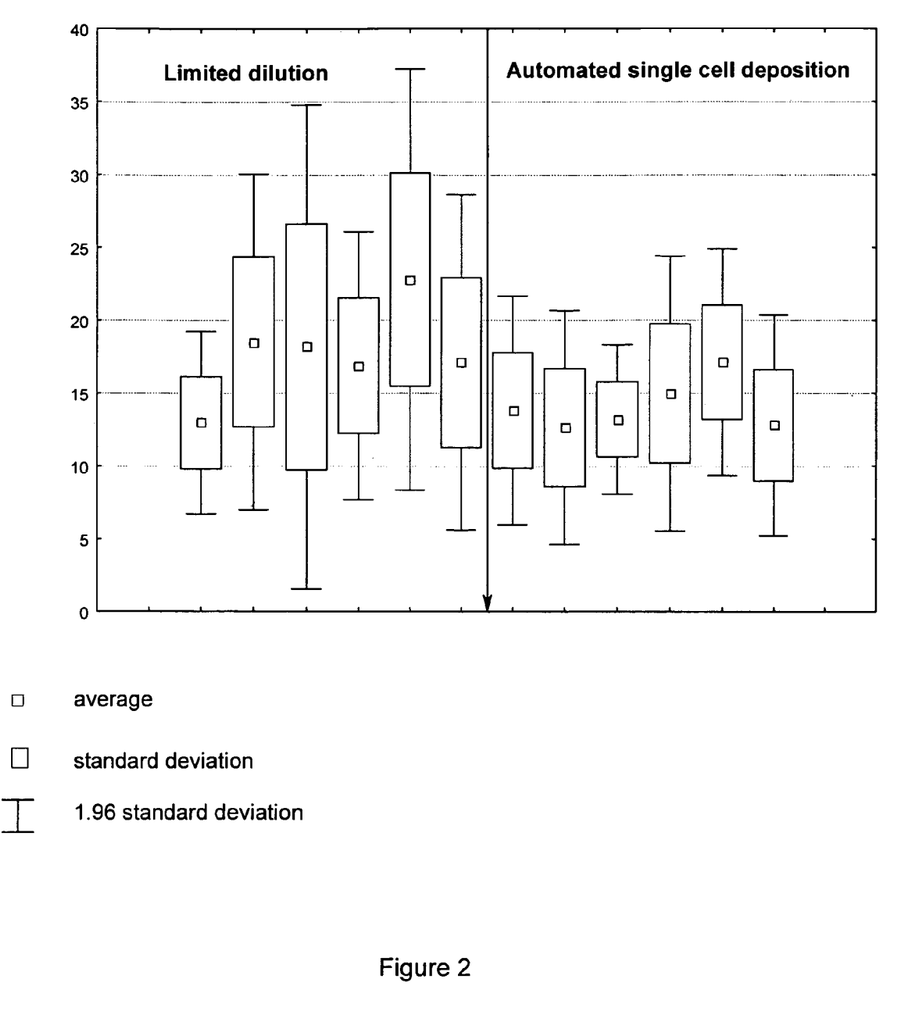
FIG. 2 shows the productivity of antibody-expressing CHO-DG44 cultures which have been obtained by limited dilution (left-hand column) or single cell deposition (right-hand column). The left-hand column shows the productivity of 6 cultures which have been obtained by limited dilution. The right-hand side shows the productivity of 6 single clones from the automated single cell deposition. To determine the productivity, three parallel experiments were carried out per cell clone/culture. In contrast to the cloning by limited dilution, cloning by automated deposition of single clones led to a substantially lower variation in the productivity. The subcultures cultivated in parallel and derived from a single clone exhibit substantially higher homogeneity with regard to their productivity compared with the subcultures obtained by limited dilution.

In order to compare the homogeneity of the cell clones, recombinant antibody-expressing CHO-DG44 cells were deposited and cloned on the one hand by the standard "limited dilution" method and on the other hand deposited and cloned by the single cell deposition method described here, in the presence of autologous feeder cells (FIG. 2). For this, six cell pools of transfected antibody-expressing CHO-DG-44 cells were cultivated by the limited dilution method and parallel after the automated single cell deposition, as described under "Culturing of the cells", and then recloned as described under "Automated single cell deposition". The clones thus produced were cultivated as described under "Culturing of the cells" and the product titre was determined over the course of three passages using the method "Determining the productivity of recombinantly expressed gene products". The average obtained from these three passages was used to plot the graph.

Example 3

High Throughput Method for Generating High-Titre Cell Clones by Combining the Expression of Fluorescent Proteins with FACS-Based Cell Sorting and FACS-Based Deposition of Single Cells By transfecting CHO DG44 cells with an expression vector which codes the bicistronic expression of a product gene (recombinant antibody) and a fluorescent protein (ZS Green from *Zoanthus* sp.), cell pools were obtained which co-express both the antibody and the fluorescent protein. These cell pools were individually deposited and cultured in microtitre plates in the presence of autologous CHO DG44 feeder cells using the method described above. The depositing of the clones was carried out using three different criteria.

A.) Depositing all the living cells
B.) Depositing the 20% most strongly fluorescent cells
C.) Depositing the 5% most strongly fluorescent cells The clones obtained were then transferred into a 24-well macrotitre plate and cultivated for three passages as described in "Cultivation of the cells". At the end of each passage the titre of the antibody in the supernatant was determined by the method described in "Determining the productivity of recombinantly expressed gene products". The average value obtained from these three passages was used to plot the graph. To do this, the number of clones obtained over defined titre categories was plotted and matched to a normal distribution.

What is claimed is:

1. A method of recloning cells, wherein fewer than 5 Chinese hamster ovary (CHO) cells are deposited in a culture vessel in the presence of irradiated autologous CHO feeder cells under serum-free conditions and cultivated and replicated under serum-free conditions, wherein the deposited CHO cells are replicated in a serum-free suspension culture and wherein the feeder cells are non-adherent feeder cells adapted to serum-free medium, wherein the recloning efficiency of said cultivation and replication of said deposited CHO cells in serum-free medium is at least 10%, wherein the deposited CHO cells are replicated in the presence of 100 to 10,000 feeder cells per ml of medium.

2. The method according to claim 1, wherein only one (1) or two (2) CHO cell(s) is or are deposited in a culture vessel under serum-free conditions and cultivated and replicated in the presence of autologous feeder cells under serum-free conditions.

3. The method according to claim 1, wherein one (1) single CHO cell is deposited in a culture vessel in the presence of autologous feeder cells under serum-free conditions and cultivated and replicated under serum-free conditions.

4. The method according to claim 1, wherein the deposited CHO cells are replicated in the presence of 500 to 10,000 feeder cells per ml of medium.

5. The method according to claim 1, wherein the deposited CHO cells are cultivated and replicated up to a density of $4 \times 10^6$ cells/ml of medium.

6. The method according to claim 1, wherein the deposited CHO cells are replicated in the presence of 2,000 to 10,000 feeder cells per ml of medium.

7. A method of recloning cells, comprising:
depositing fewer than 5 Chinese hamster ovary (CHO) cells in a culture vessel under serum-free conditions, wherein said deposited CHO cells are selected from the group consisting of CHO, CHO-K1, CHO-DUKX, CHO-DUKX B1 or CHO-DG-44 cells;
cultivating and replicating said deposited CHO cells in the presence of 100 to 10,000 irradiated autologous feeder cells per ml of medium in a serum-free suspension culture, wherein the feeder cells are non-adherent CHO feeder cells adapted to serum-free medium, and wherein the recloning efficiency of said cultivation and replication of said deposited CHO cells in serum-free medium is at least 10%.

8. The method according to claim 7, wherein the recloning efficiency of said cultivation and replication of said deposited CHO cells is at least 20%.

9. The method according to claim 7, wherein the deposited CHO cells are replicated in the presence of 500 to 10,000 feeder cells per ml of medium.

10. The method according to claim 7, wherein the deposited CHO cells are replicated in the presence of 2,000 to 10,000 feeder cells per ml of medium.

* * * * *